US006712845B2

(12) United States Patent
Hossainy

(10) Patent No.: US 6,712,845 B2
(45) Date of Patent: Mar. 30, 2004

(54) COATING FOR A STENT AND A METHOD OF FORMING THE SAME

(75) Inventor: Syed Faiyaz Ahmed Hossainy, Fremont, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 164 days.

(21) Appl. No.: 09/841,798

(22) Filed: Apr. 24, 2001

(65) Prior Publication Data

US 2002/0155212 A1 Oct. 24, 2002

(51) Int. Cl.$^7$ .................................................. A61F 2/06
(52) U.S. Cl. ...................................................... 623/1.42
(58) Field of Search .............................. 623/1.15, 1.13, 623/1.34, 1.38–1.49; 427/2.25, 2.24, 2.28

(56) References Cited

U.S. PATENT DOCUMENTS

| | | | | |
|---|---|---|---|---|
| 4,733,665 A | 3/1988 | Palmaz | ........................ | 128/343 |
| 4,800,882 A | 1/1989 | Gianturco | ........................ | 128/343 |
| 4,886,062 A | 12/1989 | Wiktor | ........................ | 128/343 |
| 4,977,901 A | 12/1990 | Ofstead | ........................ | 128/772 |
| 5,112,457 A | 5/1992 | Marchant | ........................ | 204/165 |
| 5,328,471 A | 7/1994 | Slepian | ........................ | 604/101 |
| 5,455,040 A | 10/1995 | Marchant | ........................ | 424/426 |
| 5,464,650 A | 11/1995 | Berg et al. | ........................ | 427/2.3 |
| 5,578,073 A | 11/1996 | Haimovich et al. | ........................ | 623/1 |
| 5,605,696 A | 2/1997 | Eury et al. | ........................ | 424/423 |
| 5,609,629 A * | 3/1997 | Fearnot et al. | ........................ | 623/1.42 |
| 5,667,767 A | 9/1997 | Greff et al. | ........................ | 424/9.411 |
| 5,670,558 A | 9/1997 | Onishi et al. | ........................ | 523/112 |
| 5,695,857 A | 12/1997 | Burrell et al. | | |
| 5,700,286 A | 12/1997 | Tartaglia et al. | ........................ | 623/1 |
| 5,716,981 A | 2/1998 | Hunter et al. | ........................ | 514/449 |
| 5,824,049 A | 10/1998 | Ragheb et al. | ........................ | 623/1 |
| 5,830,178 A | 11/1998 | Jones et al. | ........................ | 604/49 |

(List continued on next page.)

FOREIGN PATENT DOCUMENTS

| | | |
|---|---|---|
| EP | 0 665 023 | 8/1995 |
| EP | 0 970 711 | 1/2000 |
| WO | WO 00/12147 | 3/2000 |
| WO | WO 00/64506 | 11/2000 |
| WO | WO 01/01890 | 1/2001 |
| WO | WO 01/17577 | 3/2001 |

OTHER PUBLICATIONS

Nakayama, et al., "Surface microarchitectural design in biomedical applications: Preparation of microporous polymer surfaces by an excimer laser ablation technique", Journal of Biomedical Materials Research, vol. 29, pp. 1295–1301 (1995).

Primary Examiner—Michael J. Milano
Assistant Examiner—Tan-Uyen T. Ho
(74) Attorney, Agent, or Firm—Squire, Sanders & Dempsey, L.L.P.

(57) ABSTRACT

A coating for a stent and methods for coating a stent are provided. The coating may be used for the sustained delivery of an active ingredient or a combination of active ingredients.

45 Claims, 4 Drawing Sheets

U.S. PATENT DOCUMENTS

| | | | | |
|---|---|---|---|---|
| 5,837,313 A | 11/1998 | Ding et al. | ................ | 427/2.21 |
| 5,851,508 A | 12/1998 | Greff et al. | .............. | 424/9.411 |
| 5,858,746 A | 1/1999 | Hubbell et al. | ............. | 435/177 |
| 5,865,814 A | 2/1999 | Tuch | .......................... | 604/265 |
| 5,873,904 A | 2/1999 | Ragheb et al. | ................. | 623/1 |
| 5,895,407 A * | 4/1999 | Jayaraman | ................. | 623/1.2 |
| 5,897,911 A * | 4/1999 | Loeffler | .................... | 427/2.25 |
| 5,971,954 A | 10/1999 | Conway et al. | ................ | 604/96 |
| 5,980,928 A | 11/1999 | Terry | .......................... | 424/427 |
| 5,980,972 A | 11/1999 | Ding | ......................... | 427/2.24 |
| 6,015,541 A | 1/2000 | Greff et al. | ................ | 424/1.25 |
| 6,042,875 A | 3/2000 | Ding et al. | ................ | 427/2.24 |
| 6,051,648 A | 4/2000 | Rhee et al. | ................ | 525/54.1 |
| 6,056,993 A | 5/2000 | Leidner et al. | ............ | 427/2.25 |
| 6,060,451 A | 5/2000 | DiMaio et al. | ............... | 514/13 |
| 6,080,488 A | 6/2000 | Hostettler et al. | ....... | 428/423.3 |
| 6,096,070 A | 8/2000 | Ragheb et al. | | |
| 6,099,562 A | 8/2000 | Ding et al. | ................ | 623/1.46 |
| 6,106,889 A | 8/2000 | Beavers et al. | .............. | 427/2.1 |
| 6,110,188 A | 8/2000 | Narciso, Jr. | ................. | 606/153 |
| 6,113,629 A | 9/2000 | Ken | ........................... | 623/1.1 |
| 6,120,536 A | 9/2000 | Ding et al. | ................. | 623/1.43 |
| 6,120,904 A | 9/2000 | Hostettler et al. | ....... | 428/423.3 |
| 6,121,027 A | 9/2000 | Clapper et al. | ............. | 435/180 |
| 6,129,761 A | 10/2000 | Hubbell | ....................... | 623/11 |
| 6,153,252 A | 11/2000 | Hossainy et al. | ............. | 427/2.3 |
| 6,165,212 A | 12/2000 | Dereume et al. | .......... | 623/1.13 |
| 6,206,915 B1 * | 3/2001 | Fagan et al. | ............... | 623/1.42 |
| 6,254,632 B1 * | 7/2001 | Wu et al. | ................. | 623/1.15 |
| 6,451,373 B1 * | 9/2002 | Hossainy et al. | .......... | 427/2.25 |
| 2002/0122877 A1 * | 9/2002 | Harish et al. | | |

* cited by examiner

COATING FOR A STENT AND A METHOD OF FORMING THE SAME

BACKGROUND OF THE INVENTION

1. Field of the Invention

The invention relates to implantable devices or endoluminal prostheses, such as stents. More particularly, this invention relates to a coating for a stent and methods for making the same.

2. Description of the Background

Percutaneous transluminal coronary angioplasty (PTCA) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially press against the atherosclerotic plaque of the lesion for remodeling of the vessel wall. The balloon is then deflated to a smaller profile to allow the catheter to be withdrawn from the patient's vasculature.

A problem associated with the above procedure includes formation of intimal flaps or torn arterial linings, which can collapse and occlude the conduit after the balloon is deflated. Vasospasms and recoil of the vessel wall also threaten vessel closure. Moreover, thrombosis and restenosis of the artery may develop over several months after the procedure, which may necessitate another angioplasty procedure or a surgical by-pass operation. To reduce the partial or total occlusion of the artery by the collapse of arterial lining and to reduce the chance of the development of thrombosis and restenosis, an expandable, intraluminal prosthesis, one example of which is a stent, is implanted in the lumen to maintain the vascular patency.

Stents act as scaffoldings, functioning to physically hold open and, if desired, to expand the wall of the passageway. Typically stents are capable of being compressed, so that they can be inserted through small cavities via catheters, and then expanded to a larger diameter once they are at the desired location. Examples in the patent literature disclosing stents that have been applied in PTCA procedures include U.S. Pat. No. 4,733,665 issued to Palmaz, U.S. Pat. No. 4,800,882 issued to Gianturco, and U.S. Pat. No. 4,886,062 issued to Wiktor. Mechanical intervention via stents has reduced the rate of restenosis as compared to balloon angioplasty. Yet, restenosis is still a significant clinical problem with rates ranging from 20–40%. When restenosis does occur in the stented segment, its treatment can be challenging, as clinical options are more limited as compared to lesions that were treated solely with a balloon.

Stents are used not only for mechanical intervention but also as vehicles for providing biological therapy. Biological therapy can be achieved by medicating the stents. Medicated stents provide for the local administration of a therapeutic substance at the diseased site. In order to provide an efficacious concentration to the treated site, systemic administration of such medication often produces adverse or even toxic side effects for the patient. Local delivery is a preferred method of treatment in that smaller total levels of medication are administered in comparison to systemic dosages, but are concentrated at a specific site. Local delivery thus produces fewer side effects and achieves more favorable results. This invention provides for a stent coating capable of sustained local delivery of therapeutic substances and methods of forming the coating.

SUMMARY OF THE INVENTION

A method of coating a stent is provided. The method includes forming a first layer supported by a stent substrate and patterning the first layer by removing portions of the first layer.

In some embodiments, the method additionally includes forming a primer layer on the surface of the stent substrate prior to forming the first layer.

In other embodiments, the method includes forming a second layer on the remaining portions of the first layer. The first layer may contain a first substance and the second layer may contain a second substance different than the first substance. The first and second substances may be active ingredients, radiopaque elements, or radioactive isotopes.

In other embodiments, the act of patterning the first layer includes forming a second layer on the surface of the stent prior to forming the first layer. The second layer is patterned to form vias in the second layer. Such patterning may be performed by applying a laser discharge to selected areas of the second layer. The first layer is formed on the remaining portions of the second layer and in the vias. The second layer is patterned to remove portions of the first layer disposed on the remaining portion of the second layer to pattern the first layer.

In still other embodiments, the act of patterning the first layer includes forming a second layer on the surface of the stent prior to forming the first layer and patterning the second layer to expose portions of the surface of the stent. The act of patterning the first layer also includes forming depots in the stent between the remaining portions of the second layer, wherein the first layer fills the depots, and removing the remaining portions of the second layer to remove portions of the first layer disposed on the remaining portions of the second layer, wherein the first layer remains in the depots. A third layer may be formed on the surface of the stent and over the first layer in the depots.

In still other embodiments, the act of patterning the first layer includes forming a second layer on the first layer and patterning the second layer to form vias in the second layer to expose portions of the first layer. The act of patterning the first layer also includes removing the exposed portions of the first layer, wherein portions of the first layer positioned underneath the remaining portions of the second layer remain essentially undisturbed, and removing the remaining portions of the second layer to form a patterned first layer. A third layer may be formed on the remaining portions of the first layer.

A coated stent produced in accordance with the various methods is also provided. The coated stent includes a first layer and a discontinuous second layer separated by the first layer. The first layer is a discontinuous layer separated by the second layer so as to create an alternating pattern of the first and second layers on the surface of the stent. In accordance with another embodiment, the discontinuous first and second layers can be disposed on a primer layer.

DETAILED DESCRIPTION

"Polymer," "poly," and "polymeric" are defined as compounds that are the product of a polymerization reaction and are inclusive of homopolymers, copolymers, terpolymers etc., including random, alternating, block, and graft variations thereof. Representative examples of polymers that can be used with the embodiments of the present invention include ethylene vinyl alcohol copolymer (commonly known by the generic name EVOH or by the trade name EVAL), polyhydroxy alkanoates such as poly(hydroxyvalerate), poly(hydroxybutyrate), and poly(hydroxybutyrate-co-valerate); poly(L-lactic acid); polycaprolactone; poly(lactide-co-glycolide); polydioxanone; polyorthoester; polyanhydride; poly(glycolic acid); poly(D,L-lactic acid); poly(glycolic acid-co-trimethylene carbonate); polyphosphoester; polyphosphoester urethane; poly(amino acids); cyanoacrylates; poly(trimethylene carbonate); poly(iminocarbonate); copoly(ether-esters) (e.g., PEO/PLA); polyalkylene oxalates; polyphosphazenes and biomolecules such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon;rayon-triacetate; cellulose; cellulose acetate; cellulose butyrate; cellulose acetate butyrate; cellophane; cellulose nitrate; cellulose propionate; cellulose ethers; and carboxymethyl cellulose.

"Solvent" is defined as a liquid substance or composition which is compatible with the polymer and is capable of dissolving the polymer at the concentration desired in the composition. Examples of solvents include, but are not limited to, dimethylsulfoxide (DMSO), chloroform, acetone, water (buffered saline), xylene, methanol, ethanol, 1-propanol, tetrahydrofuran, 1-butanone, dimethylformamide, dimethylacetamide, cyclohexanone, ethyl acetate, methylethylketone, propylene glycol monomethylether, isopropanol, isopropanol admixed with water, N-methyl pyrrolidinone, toluene, and combinations thereof.

Figure 1:
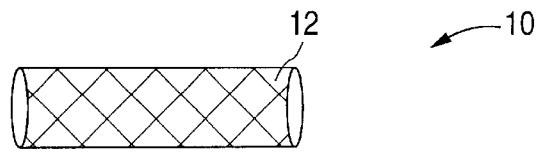
FIG. 1 illustrates a stent.

The Figures have not been drawn to scale, and the dimensions such as depth and thickness of the various regions and layers have been over or under emphasized for illustrative purposes. Referring to FIG. 1, a stent 10 is illustrated, which is broadly defined to include any inter- or intraluminal device used for the release of an active ingredient, for upholding the luminal patency, and/or for the incorporation of radiopaque or radioactive materials. Examples of stents include self-expandable stents, balloon-expandable stents, and stent-grafts. Stent 10 can be made of a metallic material or an alloy such as, but not limited to, stainless steel (316L), "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Stents made from bioabsorbable or biostable polymers could also be used with the embodiments of the present invention.

Figure 2A:
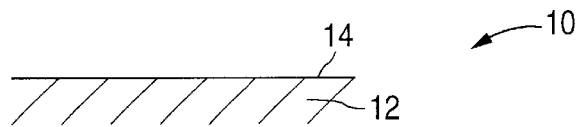
FIGS. 2A–2G illustrate a method of coating a stent in accordance with several embodiments of the invention.
Figure 2B:
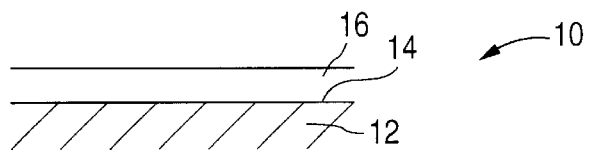

FIGS. 2A–2G illustrate a method for coating stent 10 in accordance with several embodiments of the invention. FIG. 2A illustrates a segment of the body or substrate 12 of stent 10, wherein reference number 14 denotes the outer surface or the tissue contacting surface of stent 10. The illustrations have been simplified for ease of understanding and describing the embodiments of the present invention. FIG. 2B illustrates a first layer 16 formed on substrate 12. First layer 16 can be of any suitable thickness. The thickness of first layer 16 can be from about 0.1 micron to about 20 microns, more narrowly from about 2 microns to about 10 microns. By way of example, first layer 16 can have a thickness of about 3 microns. First layer 16 can be made from a polymeric material. Polymers having a high coefficient of extinction, which allows the material to burn quickly and easily, can be used. The coefficient of extinction k is defined by Equation 1.

$$k = \{Ln(I_0/I_f)\}/h \qquad \text{(Equation 1)}$$

Where
  k=coefficient of extinction (cm$^{-1}$)
  $I_0$=initial intensity
  $I_f$=final intensity
  h=distance at final intensity (cm)

A suitably high coefficient of extinction k can be greater than or equal to 1×10$^4$ cm$^{-1}$. Examples of polymers having such a coefficient of extinction include polyimide, segmented polyurethane, and polycarbonate. Such polymers may be particularly suitable for preventing melting defects when the patterning of first layer 16 is accomplished using a laser discharge as described below.

First layer 16 can be deposited by any conventional method such as immersing substrate 12 in or spraying substrate 12 with a first composition containing a dissolved mixture of a first solvent with a first polymer and allowing the first solvent to evaporate from first layer 16. The polymer-solvent combination should be capable of forming first layer 16 as a uniform film, rather than in a powdered form, on substrate 12.

Figure 2C:
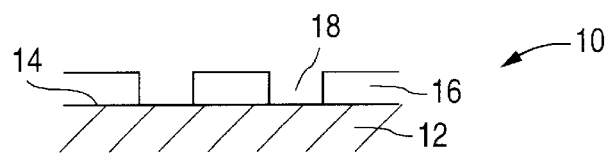

First layer 16, as illustrated in FIG. 2C, is patterned by removing or etching portions of first layer 16 to form vias 18 to expose surface 14 of substrate 12 not covered by first layer 16. Vias 18 can be formed by, for example, exposing first layer 16 to a laser discharge such as that produced by an excimer laser. The width of vias 18 is dependent on a variety of factors, such as the size of stent struts and the coating pattern that is desired. By way of example, vias 18 can be from about 5 microns to about 500 microns, for example about 100 microns wide.

Figure 2D:
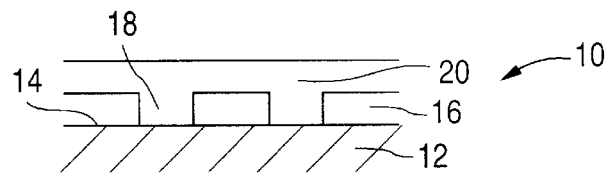

Referring to FIG. 2D, a second layer 20, containing a first substance, is deposited on substrate 12 to cover the remaining portions of first layer 16 and vias 18. Second layer 20 can be made of any suitable polymeric material and can be of any suitable thickness. The thickness of second layer 20 can be from about 0.1 micron to about 15 microns, more narrowly from about 1 micron to about 10 microns. By way of example, second layer 20 can have a thickness of about 5 microns. The polymeric material for second layer 20 should possess good adhesive qualities to surface 14 of stent 10. If a radially expandable stent 10 is used, the polymeric material should be capable of expanding with stent 10 without significant detachment or fragmenting of the material from surface 14 of stent 10. The polymeric material should be a biocompatible polymer, either bio-stable or bio-absorbable in nature. One example of such a polymer is ethylene vinyl alcohol co-polymer.

Second layer 20 can be deposited by immersing substrate 12 in or spraying substrate 12 with a second composition containing a second solvent, a second polymer, and the first substance and allowing the second solvent to evaporate. The polymer-solvent combination selected should be capable of forming second layer 20 as a uniform film, rather than in a powdered form, on substrate 12. The second solvent should be capable of placing the polymer of the second layer 20 into solution but should not be capable of removing the remaining portions of first layer 16. In other words, the second solvent should not dissolve first layer 16 during the application of the second composition.

Figure 2E:
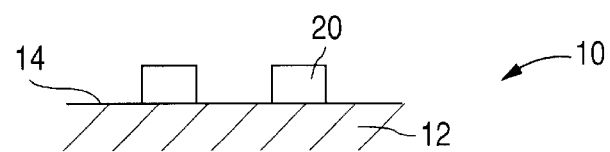

Following the application of second layer 20, the remaining portions of first layer 16 can be removed, as illustrated in FIG. 2E, to pattern second layer 20. The remaining portions of first layer 16 can be removed by the application of a solvent, such as the first solvent used to form first layer 16. The solvent should be capable of removing or dissolving the remaining portions of first layer 16. The polymeric material from which second layer 20 is made should not be capable of being dissolved during the application of the solvent. Removal of the remaining portions of first layer 16 also causes the portions of second layer 20 that are disposed over first layer 16 to be physically removed or broken-off. Portions of second layer 20 that are in contact with surface 14 remain attached to substrate 12.

Figure 2F:
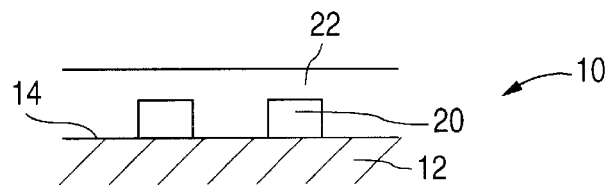
Figure 2G:
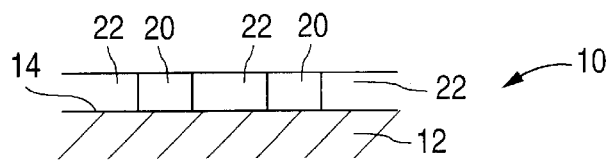

Referring to FIG. 2F, a third layer 22, containing a second substance, can be deposited on substrate 12 to cover the patterned second layer 20 and the exposed portions of surface 14. The second substance can be the same as or different than the first substance. Third layer 22 can be deposited by applying a composition containing a third solvent, the second substance, and a polymeric material to stent 10. The polymer-solvent combination selected should be capable of forming third layer 22 as a uniform film, rather than in a powdered form. The third solvent should not remove second layer 20 or adversely affect the first substance contained in the second layer 20. As an optional step, as illustrated in FIG. 2G, the profile of third layer 22 can be reduced so as to create an alternating pattern of second layer 20 and third layer 22. The resulting stent 10 includes a low profile coating defined by discontinuous second layer 20 interrupted by third layer 22. The discontinuous second layer 20 and third layer 22 can carry a first and a second substance, respectively, for release of the substances at different rates in situ.

The first and second substances can be any active ingredient capable of exerting a therapeutic or prophylactic effect in the practice of the present invention. Examples of such active ingredients include antiproliferative, antineoplastic, antiinflammatory, antiplatelet, anticoagulant, antifibrin, antithrombin, antimitotic, antibiotic, and antioxidant substances as well as combinations thereof.

A suitable example of an antiproliferative substance is actinomycin D, or derivatives and analogs thereof. Synonyms of actinomycin D include dactinomycin, actinomycin IV, actinomycin b, actinomycin $X_1$, and actinomycin $C_1$. Examples of suitable antineoplastics include paclitaxel and docetaxel. Examples of suitable antiplatelets, anticoagulants, antifibrins, and antithrombins include sodium heparin, low molecular weight heparin, hirudin, argatroban, forskolin, vapiprost, prostacyclin and prostacyclin analogs, dextran, D-phe-pro-arg-chloromethylketone (synthetic antithrombin), dipyridamole, glycoprotein IIb/IIIa platelet membrane receptor antagonist, recombinant hirudin, thrombin inhibitor (available from Biogen), and 7E-3B® (an antiplatelet drug from Centocore). Examples of suitable antimitotic agents include methotrexate, azathioprine, vincristine, vinblastine, fluorouracil, adriamycin, and mitamycin. Examples of suitable cytostatic or antiproliferative agents include angiopeptin (a somatostatin analog from Ibsen), angiotensin converting enzyme inhibitors such as CAPTOPRIL (available from Squibb), CILAZAPRIL (available from Hoffman-LaRoche), or LISINOPRIL (available from Merck), calcium channel blockers (such as Nifedipine), colchicine, fibroblast growth factor (FGF) antagonists, fish oil (omega 3-fatty acid), histamine antagonist, LOVASTATIN (an inhibitor of HMG-CoA reductase, a cholesterol lowering drug from Merck), monoclonal antibodies (such as PDGF receptors), nitroprusside, phosphodiesterase inhibitors, prostaglandin inhibitor (available form Glazo), Surmin (a PDGF antagonist), serotonin blockers, steroids, thioprotease inhibitors, triazolopyrimidine (a PDGF antagonist), and nitric oxide. Other therapeutic substances or agents which may be appropriate include alpha-interferon, genetically engineered epithelial cells, and dexamethasone. Exposure of the composition to the active ingredient is not permitted to adversely alter the active ingredient's composition or characteristic. Accordingly, the particular active ingredient is selected for compatibility with the blended polymer-solvent.

The dosage or concentration of the active ingredient required to produce a favorable therapeutic effect should be less than the level at which the active ingredient produces toxic effects and greater than the level at which non-therapeutic results are obtained. The dosage or concentration of the active ingredient required can depend upon factors such as the particular circumstances of the patient; the nature of the trauma; the nature of the therapy desired; the time over which the ingredient administered resides at the treatment site; and if other bioactive substances are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

In accordance with another embodiment, the first and/or second substances can be radiopaque elements or radioactive isotopes. Examples of radiopaque elements include, but are not limited to, gold, tantalum, and platinum. An example of a radioactive isotope is $P^{32}$. Sufficient amounts of such substances may be dispersed in the composition. By dispersed it is meant that the substances are not present in the composition as agglomerates or flocs. Certain substances will disperse with ordinary mixing, such as by stirring with a stir bar, vortexing, and similar perturbation techniques. Otherwise, the substances can be dispersed by high shear processes such as ball mill, disc mill, sand mill, attritor, rotor stator mixer, or ultrasonication—all such high shear dispersion techniques being well known to one of ordinary skill in the art. Agents in the form of surfactants, emulsifiers, or stablilizers may also be added to the composition to assist in dispersion.

Referring to FIGS. 3A–3F, an optional primer layer 24, free from any substances, can be formed on surface 14 of substrate 12 prior to the formation of first layer 16. The presence of a substance in second layer 20 can interfere with the ability of second layer 20 to adhere effectively to surface 14 of substrate 12. High drug loadings of 10–40% by weight in the matrix may significantly hinder the retention of second layer 20 on surface 14 of substrate 12. The primer layer 24 serves as a functionally useful intermediary layer between surface 14 of substrate 12 and the substance-containing second layer 20. The primer layer 24 provides for an adhesive tie which, in effect, would also allow for the quantity of the substance in the second layer 20 to be increased without compromising the ability of second layer 20 to be effectively contained on substrate 12 during delivery and, if applicable, expansion of stent 10.

With the use of thermoplastic polymers such as, but not limited to, ethylene vinyl alcohol copolymer, polycaprolactone, poly(lactide-co-glycolide), and poly(hydroxybutyrate), the deposited primer composition should be exposed to a heat treatment at a temperature range greater than about the glass transition temperature ($T_g$) and less than about the melting temperature ($T_m$) of the selected polymer. Unexpected results have been discovered with treatment of the composition under this temperature range, specifically strong adhesion or bonding of the coating to the metallic surface of a stent 10. The prosthesis should be exposed to the heat treatment for any suitable duration of time that will allow for the formation of primer layer 24 on surface 14 of substrate 12 and for the evaporation of the solvent employed.

Figure 3A:
FIGS. 3A–3F illustrate a method of coating a stent in accordance with several other embodiments of the invention.
Figure 3B:
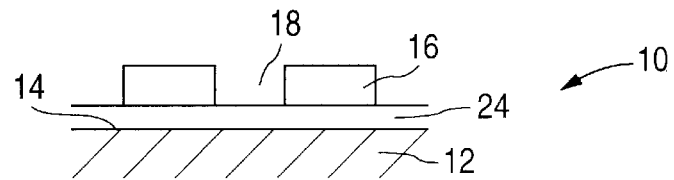
Figure 3C:
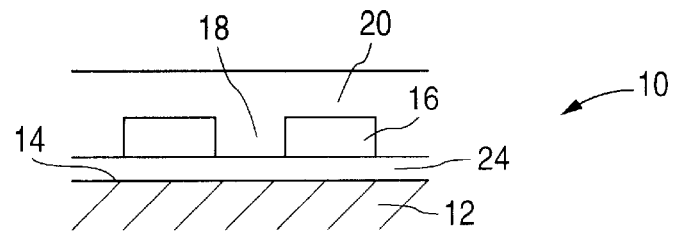
Figure 3D:
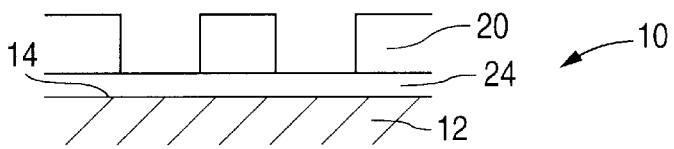
Figure 3E:
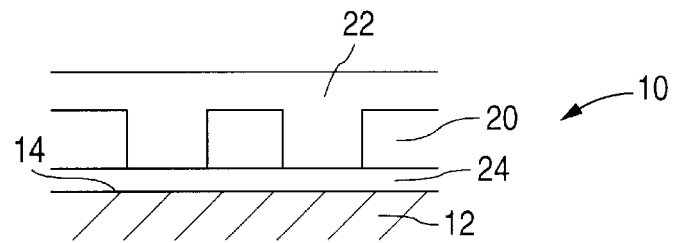
Figure 3F:
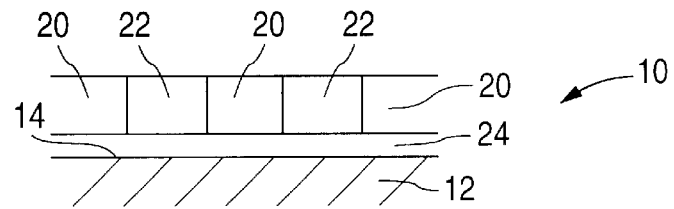

FIGS. 3A–3F correspond to the above-described FIGS. 2B–2G, respectively, but for the initial formation of primer layer 24 directly onto surface 14 of substrate 12. Briefly, FIG. 3A illustrates the formation of first layer 16 on primer layer 24. First layer 16 is patterned to form vias 18, as depicted in FIG. 3B. The underlying primer layer 24 should remain essentially undisturbed on surface 14 of substrate 12. In FIG. 3C, second layer 20, containing a first substance, is deposited on the substrate 12 to cover the remaining portions of first layer 16 and vias 18. The polymeric material selected for second layer 20 should possess good adhesive qualities to primer layer 24. Following the application of second layer 20, the remaining portions of first layer 16 are removed, as illustrated in FIG. 3D, to pattern second layer 20. Referring to FIG. 3E, a third layer 22, containing a second substance, can be deposited on second layer 20. The second substance can be the same as or different than the first substance. As an optional step, as illustrated in FIG. 3F, the profile of third layer 22 can be reduced so as to create an alternating pattern of second layer 20 and third layer 22, being adhesively tied to stent 10 via primer layer 24, and containing a combination of first and second substances that are capable of being released at different rates in situ.

Figure 4A:
FIGS. 4A–4F illustrate a method of coating a stent in accordance with several other embodiments of the invention.

FIGS. 4A–4F illustrate a method of coating stent 10 in accordance with several other embodiments of the present invention. FIG. 4A illustrates first layer 16 formed on substrate 12. First layer 16 may be made from any suitable material and can be of any suitable thickness. The thickness of first layer 16 can be from about 0.5 micron to about 10 microns, more narrowly from about 2 microns to about 8 microns. By way of example, first layer 16 can have a thickness of about 3 microns. First layer 16 can be made from a polymeric material. Polymers having a high coefficient of extinction, as discussed above, are suitable. First layer 16 can be deposited by any conventional method such as immersing substrate 12 in or spraying substrate 12 with a first composition containing a dissolved mixture of a first solvent with the polymer and allowing the first solvent to evaporate from first layer 16.

Figure 4B:
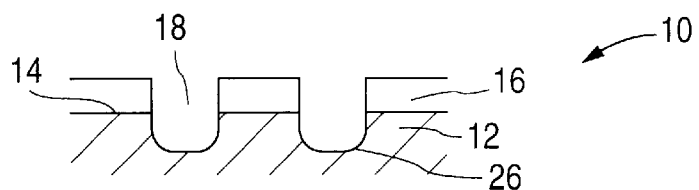

First layer 16, as illustrated in FIG. 4B, is patterned by removing or etching portions of first layer 16 to form vias 18. Additionally, portions of substrate 12 underlying the removed portions of first layer 16 are removed or etched to form depots 26. Depots 26 can be formed by, for example, exposing first layer 16 and the underlying substrate 12 to a laser discharge such as that produced by an excimer laser.

Figure 4C:
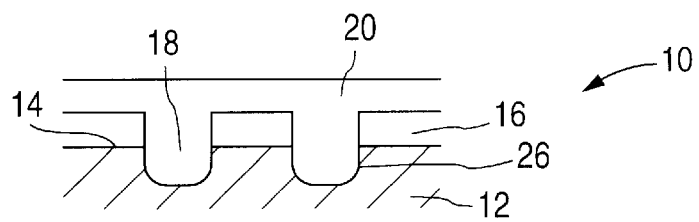

Referring to FIG. 4C, a second layer 20, containing a first substance, is deposited on the substrate 12 to fill depots 26 and vias 18 and to cover the remaining portions of first layer 16. Second layer 20 can be made of a polymeric material having good adhesive qualities to substrate 12. One example of such a polymer is ethylene vinyl alcohol co-polymer.

Figure 4D:
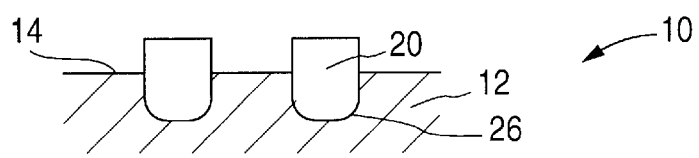
Figure 4E:
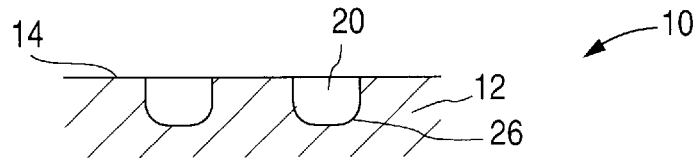

Following the application of second layer 20, the remaining portions of first layer 16 are removed, as illustrated in FIG. 4D, to pattern second layer 20. The remaining portions of first layer 16 can be removed by the application of a solvent, such as the first solvent used to form first layer 16. The polymeric material from which second layer 20 is made should not be capable of being removed or dissolved during the application of the solvent. Removal of the remaining portions of first layer 16 also causes the portions of second layer 20 that are disposed over first layer 16 to be physically removed or broken-off. Portions of second layer 20 that are within depots 26 remain attached to substrate 12. As illustrated in FIG. 4E, the profile of second layer 20 can be reduced so as to remove the portions of second layer 20 extending above surface 14.

Figure 4F:
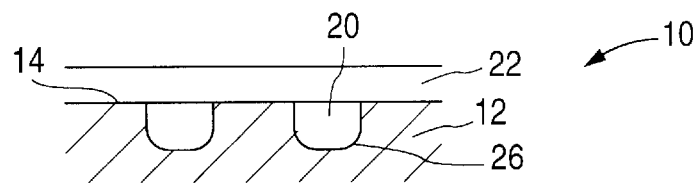

Referring to FIG. 4F, in accordance with another embodiment, a third layer 22 containing a second substance, can be deposited on substrate 12 to cover second layer 20 within depots 26 as well as surface 14. The second substance can be the same as or different than the first substance. Third layer 22 can be made of any suitable polymeric material and can be of any suitable thickness. The thickness of third layer 22 can be from about 0.2 microns to about 10 microns, more narrowly from about 2 microns to about 8 microns. By way of example, third layer 22 can have a thickness of about 5 microns. The resulting stent 10 includes a first substance within depots 26 and a second substance in third layer 22, each of which is capable of being released at a different rate in situ.

Figure 5A:
FIGS. 5A–5H illustrate a method of coating a stent in accordance with several other embodiments of the invention.
Figure 5B:
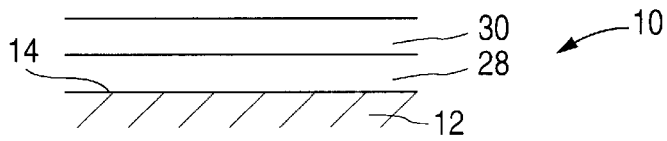

FIGS. 5A–5H illustrate a method of coating stent 10 in accordance with other embodiments of the present invention. FIG. 5A illustrates a first layer 28, containing a first substance. The thickness of first layer 28 can be from about 0.2 micron to about 10 micron, more narrowly from about 2 microns to about 8 microns. By way of example, first layer 28 can have a thickness of about 5 microns. FIG. 5B illustrates a second layer 30 formed on substrate 12 to cover first layer 28. The thickness of second layer 30 can be from about 1 micron to about 10 microns, more narrowly from about 2 microns to about 8 microns. By way of example, second layer 30 can have a thickness of about 4 microns. Second layer 30 can be made from a polymeric material such as, but not limited to, polyurethanes or parylene.

Figure 5C:
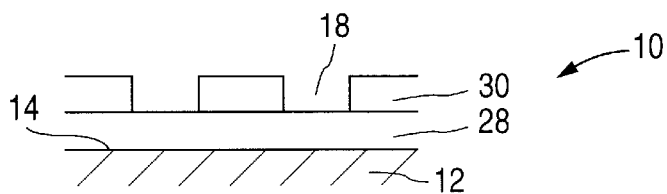
Figure 5D:
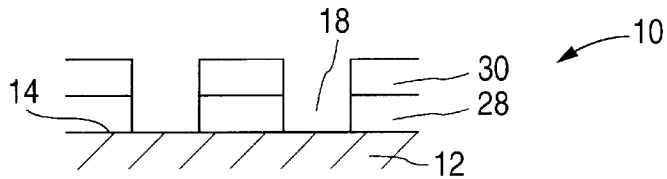

Second layer 30, as illustrated in FIG. 5C, is patterned by removing portions of second layer 30 to form vias 18 to expose portions of first layer 28 not covered by second layer 30. Vias 18 can be formed by, for example, exposing second layer 30 to a laser discharge. First layer 28 is patterned by removing portions of first layer 28 not covered by the remaining portions of second layer 30, as illustrated in FIG. 5D. First layer 28 can be pattered by exposing the uncovered portions of first layer 28 to a solvent so as to remove or dissolve the selected portions of first layer 28.

Figure 5E:
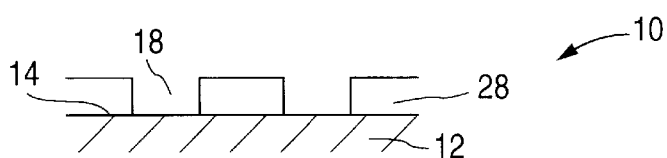

The remaining portions of second layer 30 can be removed, as illustrated in FIG. 5E by, for example, exposing second layer 30 to a laser discharge. Alternatively, the remaining portions of second layer 30 can be removed by the application of a solvent. The solvent should be capable of removing or dissolving the remaining portions of second layer 20, but should not remove the polymeric material from which first layer 28 is made or adversely affect the first substance.

Figure 5F:
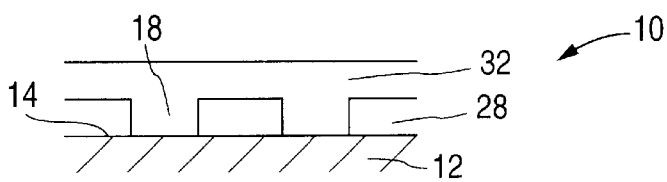

Referring to FIG. 5F, a third layer 32, containing a second substance, is deposited on substrate 12 to cover the remaining portion of first layer 28 and vias 18. Third layer 32 can be made of any suitable polymeric material and can be of any suitable thickness. The solvent used to form third layer 32 should be capable of placing the polymer of the third layer 32 into solution, but should not be capable of removing the remaining portions of first layer 28. In other words, the solvent should not dissolve first layer 28 during the application of the third solution.

Figure 5G:
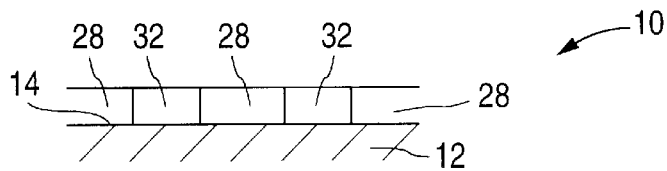
Figure 5H:
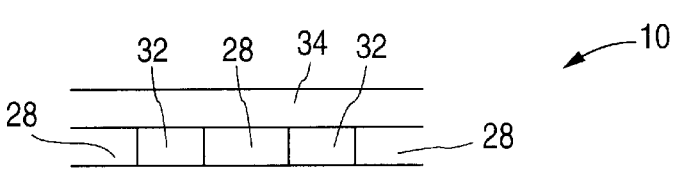

Following the application of third layer 32, the profile of third layer 32 can optionally be reduced so as to create an alternating pattern of first layer 28 and third layer 32 having essentially the same thickness, as depicted in FIG. 5G. As another optional step, a fourth layer 34 can be deposited on the alternating pattern of first layer 28 and third layer 32, as illustrated in FIG. 5H. In some embodiments, fourth layer 34 functions as a diffusion barrier for the first and second substances in first layer 28 and third layer 32, respectively. Fourth layer 34 can also contain a third substance. The third substance can be the same as or different than the first and second substances. The resulting stent 10 includes a low profile coating having a combination of first, second and third substances that are capable of being released at different rates in situ. In yet another embodiment, a primer layer (not shown) can also be employed.

In the above-described embodiments, high temperature heating in a furnace (e.g., 700–800° C.) may be employed to incinerate all polymers on substrate 12. This polymer removal technique is particularly suitable when gold or platinum has been deposited as the first substance.

In accordance with the above-described methods, one or more active ingredient can be applied to a device, e.g., a stent, retained on the stent during delivery and expansion of the stent, and released at a desired control rate and for a predetermined duration of time at the site of implantation. A stent having the above-described coating is useful for a variety of medical procedures, including, by way of example, treatment of obstructions caused by tumors in bile ducts, esophagus, trachea/bronchi and other biological passageways. A stent having the above-described coating is particularly useful for treating occluded regions of blood vessels caused by abnormal or inappropriate migration and proliferation of smooth muscle cells, thrombosis, or restenosis. Stents may be placed in a wide array of blood vessels, both arteries and veins. Representative examples of sites include the iliac, renal, and coronary arteries.

Briefly, an angiogram is first performed to determine the appropriate positioning for stent therapy. Angiography is typically accomplished by injecting a radiopaque contrast agent through a catheter inserted into an artery or vein as an x-ray is taken. A guidewire is then advanced through the lesion or proposed site of treatment. Over the guidewire is passed a delivery catheter which allows a stent in its collapsed configuration to be inserted into the passageway. The delivery catheter is inserted either percutaneously or by surgery into the femoral artery, brachial artery, femoral vein, or brachial vein, and advanced into the appropriate blood vessel by steering the catheter through the vascular system under fluoroscopic guidance. A stent having the above-described coating may then be expanded at the desired area of treatment. A post insertion angiogram may also be utilized to confirm appropriate positioning.

While particular embodiments of the present invention have been shown and described, it will be obvious to those skilled in the art that changes and modifications can be made without departing from this invention in its broader aspects and, therefore, the appended claims are to encompass within their scope all such changes and modifications as fall within the true spirit and scope of this invention.

What is claimed is:

1. A method of coating a stent, comprising:
   (a) forming a first layer on a surface of a stent;
   (b) patterning said first layer to form vias by removing portions of said first layer;
   (c) forming a second layer to cover the remaining portions of said first layer and to at least partially fill said vias; and
   (d) removing the remaining portions of said first layer to form a pattern of said second layer on said surface of said stent.

2. A coated stent produced in accordance with the method of claim 1.

3. The method of claim 1, additionally comprising forming a third layer on the remaining portions of said second layer.

4. The method of claim 3, wherein said second layer contains a first substance and said third layer contains a second substance different than said first substance.

5. The method of claim 4, wherein said first or second substances are selected from a group of therapeutic agents, radiopaque elements and radioactive isotopes.

6. The method of claim 3, wherein said second layer comprises a therapeutic agent and said third layer is configured to be a diffusion barrier for said therapeutic agent.

7. The method of claim 1, wherein said first layer comprises a polymer.

8. The method of claim 7, wherein said polymer has a coefficient of extinction k equal to or greater than $1 \times 10^4$ cm$^{-1}$.

9. The method of claim 1, wherein said first layer comprises a polymer selected from the group consisting of polyimide, segmented polyurethane and polycarbonate.

10. The method of claim 1, wherein patterning said first layer to form vias comprises directing a laser discharge to said first layer.

11. The method of claim 1, wherein said vias have a width of about 5 microns to about 500 microns.

12. The method of claim 1, wherein said second layer comprises a polymer and optionally a therapeutic agent.

13. A method of coating a stent, comprising:
   (a) forming a primer layer on a surface of a stent substrate;
   (b) forming a first layer on said primer layer;
   (c) patterning said first layer to form vias in said first layer, wherein said primer layer remains essentially undisturbed on the surface of said stent substrate;
   (d) forming a second layer on the remaining portions of said first layer and in said vias on said primer layer; and
   (e) removing the remaining portions of said first layer to remove portions of said second layer disposed on the remaining portions of said first layer to pattern said second layer.

14. The method of claim 13, wherein said primer layer or said first layer comprises a polymer.

15. The method of claim 14, wherein said polymer has a coefficient of extinction k equal to or greater than $1 \times 10^4$ cm$^{-1}$.

16. The method of claim 13, wherein said first layer comprises a polymer selected from the group consisting of polyimide, segmented polyurethane and polycarbonate.

17. The method of claim 13, wherein patterning said first layer to form vias comprises directing a laser discharge to said first layer.

18. The method of claim 13, wherein said vias have a width of about 5 microns to about 500 microns.

19. The method of claim 13, wherein said second layer comprises a polymer and optionally a therapeutic agent.

20. A method of coating a stent, comprising:
   (a) forming a first layer on the surface of a stent;
   (b) patterning said first layer to expose portions of the surface of said stent;
   (c) forming depots in said stent between the remaining portions of said first layer;
   (d) forming a second layer on said stent, wherein said second layer fills said depots; and
   (e) removing the remaining portions of said first layer to remove portions of said second layer disposed on the remaining portions of said first layer, wherein said second layer remains in said depots.

21. The method of claim 20, additionally comprising reducing the profile of said second layer such that said second layer does not protrude out from said depots.

22. The method of claim 20, additionally comprising forming a third layer over said second layer and on the surface of said stent.

23. The method of claim 22, wherein said second layer comprises a therapeutic agent and said third layer is configured to be a diffusion barrier for said therapeutic agent.

24. The method of claim 22, wherein said second layer contains a first substance and said third layer contains a second substance different from said first substance.

25. The method of claim 20, wherein said first layer comprises a polymer.

26. The method of claim 20, wherein said polymer has a coefficient of extinction k equal to or greater than $1 \times 10^4$ cm$^{-1}$.

27. The method of claim 20, wherein said first layer comprises a polymer selected from the group consisting of polyimide, segmented polyurethane and polycarbonate.

28. The method of claim 20, wherein patterning said first layer comprises directing a laser discharge to said first layer.

29. The method of claim 20, wherein said second layer comprises a polymer and optionally a therapeutic agent.

30. The method of claim 20, wherein forming depots in said stent comprises directing a laser discharge to the surface of said stent.

31. A method of coating a stent, comprising:
   (a) forming a first layer on a stent;
   (b) forming a second layer on said first layer;
   (c) patterning said second layer to form vias in said second layer to expose portions of said first layer;
   (d) removing the exposed portions of said first layer, wherein portions of said first layer positioned underneath the remaining portions of said second layer remain essentially undisturbed; and
   (e) removing the remaining portions of said second layer to form a patterned first layer.

32. The method of claim 31, additionally comprising forming a third layer on the remaining portions of said first layer.

33. The method of claim 32, additionally comprising reducing the profile of said third layer so as to create an alternating pattern of said first layer and said third layer.

34. The method of claim 32, wherein said first layer contains a first substance and said third layer contains a second substance different from said first substance.

35. The method of claim 34, wherein the said first and second substances are therapeutic agents.

36. The method of claim 32, wherein said first layer is a discontinuous layer interrupted by said third layer.

37. The method of claim 32, wherein said first layer comprises a therapeutic agent and said third layer is configured to be a diffusion barrier for said therapeutic agent.

38. The method of claim 31, wherein said second layer comprises a polymer.

39. The method of claim 38, wherein said polymer has a coefficient of extinction k equal to or greater than $1 \times 10^4$ cm$^{-1}$.

40. The method of claim 31, wherein said second layer comprises polyurethane or parylene.

41. The method of claim 31, wherein patterning said second layer to form vias comprises directing a laser discharge to said second layer.

42. The method of claim 31, wherein said vias have a width of about 5 microns to about 500 microns.

43. The method of claim 31, wherein said first layer comprises a polymer and optionally a therapeutic agent.

44. A method of coating a stent, comprising:
   (a) forming a primer layer on a surface of a stent substrate;
   (b) forming a first layer on said primer layer;
   (c) patterning said first layer to form vias in said first layer, wherein said primer layer remains essentially undisturbed on the surface of said stent substrate; and
   (d) forming a second layer on the remaining portions of said first layer and in said vias on said primer layer.

45. A method of coating an implantable medical device, comprising:
   (a) forming a first layer on an implantable medical device;
   (b) forming a second layer on said first layer;
   (c) patterning said second layer to form vias in said second layer to expose portions of said first layer;
   (d) removing the exposed portions of said first layer, wherein portions of said first layer positioned underneath the remaining portions of said second layer remain essentially undisturbed; and
   (e) removing the remaining portions of said second layer to form a patterned first layer.

* * * * *